United States Patent [19]

Riedhammer et al.

[11] Patent Number: 4,820,352

[45] Date of Patent: Apr. 11, 1989

[54] CLEANING AND CONDITIONING SOLUTIONS FOR CONTACT LENSES AND METHODS OF USE

[75] Inventors: Thomas M. Riedhammer, Rochester; Francis X. Smith, Walworth, both of N.Y.

[73] Assignee: Bausch & Lomb Incorporated, Rochester, N.Y.

[21] Appl. No.: 821,228

[22] Filed: Jan. 22, 1986

Related U.S. Application Data

[63] Continuation of Ser. No. 730,907, May 6, 1985, abandoned, which is a continuation of Ser. No. 456,960, Jan. 10, 1983, abandoned.

[51] Int. Cl.$^4$ .................. C11D 1/44; C11D 3/48; B08B 30/00
[52] U.S. Cl. ........................... 134/30; 134/26; 134/42; 252/106; 252/173; 252/174.21; 252/548; 252/DIG. 14; 514/839
[58] Field of Search ....... 252/106, 173, 548, DIG. 14; 134/42, 30, 26; 514/839, 840; 752/174.21

[56] References Cited

U.S. PATENT DOCUMENTS

| | | | |
|---|---|---|---|
| 3,882,036 | 5/1975 | Krezanoski et al. | 252/106 |
| 3,884,826 | 5/1975 | Phares et al. | 252/106 |
| 3,954,644 | 5/1976 | Krezanoski et al. | 252/106 |
| 4,029,817 | 6/1977 | Blanco et al. | 424/329 |
| 4,048,122 | 9/1977 | Sibley et al. | 252/541 |
| 4,127,423 | 11/1978 | Rankin | 134/30 |
| 4,323,467 | 4/1982 | Fu | 252/106 |
| 4,388,229 | 6/1983 | Fu | 252/549 |
| 4,440,662 | 4/1984 | Tsuzuki et al. | 252/106 |

*Primary Examiner*—Prince E. Willis
*Attorney, Agent, or Firm*—Bernard D. Bogdon; Craig E. Larson

[57] ABSTRACT

Contact lens cleaning compositions comprising preserved surfactant-containing solutions of a poly(oxypropylene)-poly(oxyethylene) adduct of ethylene diamine having a molecular weight from about 7500 to as high as 27,000 wherein at least 40 weight percent of the adduct is poly(oxyethylene) hydrophilic units. The solutions are effective in removing protein/lipid tear film deposits on both hard and soft contact lenses while providing a prophylactic-like action in retarding the formation of subsequent tear film deposits. The compositions provide effective cleaning and conditioning action using both ambient and high temperature disinfection methods.

19 Claims, No Drawings

CLEANING AND CONDITIONING SOLUTIONS FOR CONTACT LENSES AND METHODS OF USE

This application is a continuation of application Ser. No. 730,907, filed May 6, 1985 and of application Ser. No. 456,960 filed Jan. 10, 1983, both now abandoned.

BACKGROUND OF THE INVENTION

This invention relates generally to improved contact lens cleaning and conditioning solutions for removing and inhibiting build-up of tear film deposits and debris on lens surfaces.

In addition to the foregoing, the solutions of the present invention have improved versatility in being adaptable for most contact lens cleaning processes ranging from room temperature cleaning to high temperature disinfecting without adversely affecting the physical characteristics of the lenses.

When contact lenses are removed from the eyes, they lose water and retain on their surface a deposit or proteinaceous oily and sebaceous matter which, if not removed, greatly reduces wettability properties and optical clarity of the lenses. In the case of hard contact lenses fabricated from poly(methyl methacrylate), they are of such firmness the lenses can be treated with mechanical devices to remove deposits of contamination from their surfaces. Likewise, because hard contact lenses do not absorb appreciable amounts of water, the selection of cleaning agents is relatively non-critical. In many instances, use of even harsh disinfecting and cleaning agents on hard contact lenses does not create a problem.

However, because of the hydrophilic properties of soft contact lenses formulated from materials like poly(-hydroxyethyl methacrylate), they do absorb more water than hard contact lenses. Consequently, greater care must be exercised in formulating cleansing solutions for soft contact lenses because materials in the solutions can be absorbed and concentrated in the lenses which in-turn can damage the lens and even injure the eyes of the user.

In many instances, solutions intended for hard contact lenses are generally not adaptable for use with soft contact lenses. This may be illustrated, for instance, in the case of hard contact lens solutions containing benzalkonium chloride or chlorobutanol, if used on soft contact lenses their important hydrophilic properties may be lost. Thus, in formulating contact lens care solutions, such as cleaning compositions, a number of factors need to be carefully weighed to assure total compatibility of the system in terms of functional efficaciousness, potential for damage to the lens and possible hazards to the wearer's eyes.

Various contact lens care formulations have been described in the literature, including the following patents: U.S. Pat. Nos. 4,323,467; 3,882,036; 3,954,644; 3,884,826; 4,127,423. U.S. Pat. No. 4,323,467 to Fu discloses an all-purpose type solution for storing, cleaning or wetting contact lenses containing a poly(oxyethylene)-poly(oxypropylene) substituted ethylene diamine surfactant having a molecular weight of between 1600 and 27,000; a germicidal agent; a viscosity builder; a tonicity agent and sequestering agent. Fu suggests, in essence, that any member of the family of surfactants, available from BASF-Wyandotte under the registered trademark Tetronic, may be employed in contact lens care solutions. However, little, if any, information is provided identifying which specific surfactants within the broad class may be used at the lowest concentration to assure optimal cleaning efficiencies and lens compatibility while minimizing the potential for eye irritation. Non-irritating amounts of surfactant up to as high as 40 percent by weight are recommended. It is also significant that viscosity builders are required by the patentee to maintain a film of surfactant on the surface of the lens for enhanced comfort and wearability. However, it was discovered that viscosity builders have the disadvantage of making the lens cleaning process more difficult. Because of increased adherence, the cleaning compositions resist removal during final washing, increasing the risk of residue build-up and incidence of eye tissue irritation.

U.S. Pat. Nos. 3,882,036 and 3,954,644 to Krezanoski et al also suggest all-purpose type care solutions for contact lenses containing poly(oxyethylene)-poly(oxypropylene) block copolymer surfactants available under the registered trademark Pluronic. These surfactants are not adducts of ethylene diamine.

U.S. Pat. No. 3,884,826 to Phares et al disclose a gel type cleaner for hard contact lenses containing various non-ionic surfactants commercially available under well-known trademarks, like Tweens, Spans, Myrj, Brij, Pluronics, etc. These non-ionic cleaners, however, do not provide the capability of wide temperature range cleaning needed for removal of tear film buildup on lenses or prophylactic conditioning of lenses.

As in a number of the foregoing patent publications, U.S. Pat. No. 4,127,423 to Rankin discloses contact lens cleaning solutions also containing inter-alia non-ionic surfactant, such as Pluronics, along with tonicity agents, viscosity agents, detergents and bactericides. Such additives will not increase the cleaning efficiency spectrum of surfactant based contact lens cleaners, and may only compound lens compatibility problems and possible risk of materials being absorbed and concentrated in the lenses increasing the risk of eye irritation. Accordingly, there is a need for improved cleaning and conditioning solutions which are efficient in removing proteinaceous and lipid tear-film build-up and also control the rate of subsequent film development while being compatible with both soft and hard contact-lenses, and perform effectively under most cleaning process conditions.

The present invention provides an improved means for both removing and inhibiting the natural build-up of film development on contact lenses, and is particularly compatible with soft type contact lenses while minimizing both the potential risk of damage to lenses and the occurrence of eye irritation. The cleaning solutiosn are specially noteworthy in they are exceptionally efficient in dispersing proteinaceous and lipid-containing tear film deposits effectively at wide temperature ranges making them readily adaptable to virtually any cleaning process.

SUMMARY OF THE INVENTION

In accordance with this invention, there is provided an aqueous solution which effectively cleans and prophylactically conditions contact lenses at both ambient and elevated temperature conditions when contacted for a sufficient time period to remove build-up of tear film deposits and surface debris, the solution consisting essentially of from about 0.01 to about 15 weight percent of poly(oxypropylene)-poly(oxyethylene) adduct of ethylene diamine having a molecular weight from about 7500 to about 27,000 wherein at least 40 weight percent of said adduct is poly(oxyethylene). Solutions disclosed herein will contain preservatives to maintain product sterility. In addition, the tonicity and pH of the cleaning and conditioning solutions, for example, may be adjusted by the addition of isotonic saline and buffering agents.

DESCRIPTION OF THE PREFERRED EMBODIMENTS

This invention relates to cleaning and conditioning solutions which are compatible for use with most contact lenses, including hard and soft lenses, as well as the newer hard gas permeable type contact lenses, such as described in U.S. Pat. No. 4,327,203. The term "soft contact lens" as used herein generally refers to those contact lenses which readily flex under small amounts of force and return to their original shape when that force is released. Typically, soft contact lenses are formulated from poly(hydroxyethyl methacrylate) which has been, in the preferred formulations, cross-linked with ethylene glycol dimethacrylate. For convenience, this polymer is generally known as PHEMA. Soft contact lenses are also made from silicon polymers cross-linked, for example, with dimethyl polysiloxane Conventional "hard contact lenses", which cover only the cornea of the eye, usually consists of poly(methyl methacrylate) cross-linked with ethylene glycol dimethacrylate.

The cleaning compositions of the present invention are particularly useful for removing and dispersing protein and lipid-containing film deposits which adhere to contact lens surfaces. In addition, the solutions of the immediate invention are also effective in conditioning lenses by providing a prophylactic-like action on lens surfaces retarding the rate and level of tear film development.

One embodiment of the aqueous contact lens cleaning and conditioning compositions comprises a block copolymer adduct of ethylene diamine non-ionic surfactant. The surfactant is a poly(oxypropylene)-poly(oxyethylene) block copolymer adduct of ethylene diamine having a molecular weight from about 10,000 to about 20,000 where at least 40 weight percent, and more particularly, from about 40 to about 80 weight percent of the surfactant is poly(oxyethylene). More preferably, the poly(oxypropylene)-poly(oxyethylene) block copolymer adduct will have a molecular weight ranging from about 12,000 to about 19,000 where at least 60 weight percent, and more particularly, from about 60 to 80 weight percent of the adduct is poly(oxyethylene).

The foregoing surfactants are further described with methods for their manufacture in U.S. Pat. No. 2,979,528. They are also known by the generic name—poloxamine—and are commercially available from BASF-Wyandotte under the registered trademark—Tetronic—. For convenience purposes, the surfactants employed in the cleaning and conditioning solutions disclosed herein will be referred to as Tetronic generally, and with a numerical suffix to identify a particular grade of material.

There are some 21 grades of Tetronic surfactants available with molecular weights ranging from as low as 1650 to 27,000. Properties of each grade within the series will vary depending on the percent of hydrophilic units poly(oxyethylene) and molecular weight of hydrophobic units poly(oxypropylene) in the adduct. Notwithstanding that all members within the series exhibit wetting and detergency properties, it was discovered that only certain members are suitable for use in the cleaning and conditioning solutions disclosed herein, due to the wide variation in performance characteristics regulated by their hydrophilic-hydrophobic balance. That is to say, the Tetronic surfactants found suitable are those capable of demonstrating maximum cleaning efficiency in dispersing both protein and lipid deposits at ambient and elevated temperatures at lowest solution concentration without trade-offs in lens compatibility and toxicity levels, i.e. maintaining lowest potential as an irritant to eye tissues. To illustrate, Tetronic surfactants having molecular weights of less than 7500 and having hydrophilic chains of about 10 weight percent poly(oxyethylene) units have the most effective detergent properties, but are substantially immiscible in aqueous solutions at 25° C. Consequently, Tetronic Series 701 through 1501 would be unsuitable for use in the aqueous contact lens cleaning solutions described herein. Similarly, solutions having only 20 weight percent hydrophilic units like Tetronic 702; 1102; 1302 and 1502 although miscible in aqueous medium and possessing superior detergency properties, they nevertheless, were found to have too high a potential for irritating eye tissues.

Accordingly, it has been discovered that maximum cleaning efficiency in dispersing both proteinaceous and lipid film deposits, as well as inhibiting film formation, on contact lenses with little or no potential for irritation to eye tissues may be achieved with solid grades of tetronic surfactant, particularly those having from about 60 to about 80 percent by weight poly(oxyethylene) hydrophilic units. These preferred embodiments include Tetronic 707; 1107 and 1307. Furthermore, because of their very hydrophilic properties, they remain in solution and do not become turbid.

The aqueous cleaning and conditioning solutions provide efficient performance at concentrations ranging from as little as 0.01 to about 15 weight percent. Greater concentrations may be used, but provide no added benefit and only increase the potential for irritating eye tissues. More preferably, the solutions of the subject invention will contain from about 0.1 to about 5 weight percent surfactant.

In order to preserve the sterility of the aqueous solutions described herein, small, but effective amounts of a antibacterial agent is required to provide antimicrobial effect, and include such agents as thimerosal, 1,5-pentanedial, alkyl triethanolamine, benzalkonium chloride, sorbic acid, phenylmercuric salts, e.g. nitrate, borate, acetate, chloride and mixtures thereof. Other antibacterial compounds and salts may be used, such as chlorhexidine (1,1'-hexamethylene-bis [5-(p-chlorophenyl) biguanide]) or its water soluble salts. Suitable salts of chlorhexidine are soluble in water at ambient temperature to the extent of at least 0.5 weight percent. These salts include the gluconate, isothionate (2-hydroxyethanesulfonate), formate, acetate, glutamate, succinamate, monodiglycollate, dimethanesulfonate, lactate, diisobutyrate and glucoheptonane. Typically, preservatives will be used in an amount from about 0.001 to about 0.5 weight percent.

No further ingredients need be added to the preserved aqueous cleaning and conditioning solutions previously described. For example, the compositions of the present invention should be free or virtually free of agents which act specifically to thicken or increase the viscosity, or in other words, inhibit easy removal of the solution from lenses during the final rinsing step of a cleaning process. For purposes of the present invention, the expression "consisting essentially of" as used herein and in the claims means only those ingredients expressly recited plus inactive ingredients, including thickening agents in minor amounts which do not materially alter the viscosity of the solution, and excluding thickening agents which do materially alter the viscosity.

Notwithstanding the foregoing, in addition to the active ingredients previously described, tonicity agents, buffers and sequestering agents may be optionally employed. In this regard, added materials must be nontoxic and must not distort the lens. For example, inadvertently should the cleaning and conditioning solution not be washed from the lens after use, lens discomfort to the wearer can be avoided if the tonicity of the solution is modified to that of lacrimal fluids. Thus, the tonicity of the solution may be adjusted with 0.9 percent saline.

In order to maintain the pH of the cleaning and conditioning solutions within the range of about 6.5 to 7.8, suitable buffers may be added, such as boric acid, sodium borate, potassium citrate, citric acid, sodium bicarbonate, including combinations of $Na_2HPO_4$, $NaH_2PO_4$ and $KH_2PO_4$. Generally, buffers will be used in amounts ranging from about 0.05 to 2.5, and preferably, from 0.1 to 1.5 percent (w/v).

In addition to tonicity and buffering agents, in some instances it may be desirable to include sequestering agents to the cleaning and conditioning solutions in order to bind metal ions which might otherwise react with protein deposits and collect on the lens. Ethylenediaminetetraacetic acid (EDTA) and its salts (disodium) are preferred examples. They are usually added in amounts ranging from about 0.1 to about 2.0 weight percent.

The aqueous cleaning and conditioning solutions may be effectively used in removing and dispersing protein and lipid tear film deposits on both hard and soft type contact lenses by any of the well-recognized methods. For example, when the wearer of contact lenses removes them from the eyes, the lens may be rubbed with the cleaning solution followed by "cold" soaking at room temperature for a period ranging from about four to twelve hours. The lenses are then removed from the solution, washed in preserved isotonic saline solution and then replaced on the eyes.

When the cleaning process includes a rinsing step, however, the cleaning solution may contain higher concentrations of surfactant, e.g. 5 to 15 weight percent. However, the rinsing step may be omitted when, for example, the cleaning solution contains up to 0.5 weight percent of surfactant. In addition to the cold soaking method, the solutions disclosed herein are adaptable for use in other type of equipment such as ultrasonic cleaners. Furthermore, because the solutions are also stable when heated to temperatures in the range of 80° to 90° C. They are also adaptable for use with high temperature disinfecting methods. Typically, lenses are heated to 80° C. in a disinfecting unit containing the cleaning and conditioning solution for a time period of at least 10 minutes, removed and rinsed with isotonic saline.

The following specific examples demonstrate the compositions and methods of the instant invention. However, it is to be understood that these examples are for illustrative purposes only and do not purport to be wholly definitive as to conditions and scope.

EXAMPLE I

An aqueous contact lens cleaning and conditioning solution was prepared having the following formulation:

|  | Grams |
| --- | --- |
| Tetronic 1107* | 1.000 |
| Sodium Chloride | 6.750 |
| Boric Acid | 4.420 |
| Sodium Borate | 0.875 |
| $Na_2$ EDTA | 1.000 |
| Thimerosal (10 ppm) | 0.010 |
| Dist. Water qs | 1 liter |

*Flake grade, molecular weight 14,500, 70% (wt.) poly(oxyethylene)

The solution was prepared by dissolving the sodium borate in 800 ml of distilled water. The disodium EDTA was then added to the sodium borate solution, followed by dissolving the boric acid and sodium chloride therein. The Tetronic surfactant was subsequently added to the solution, but vigorous stirring was avoided to limit foam development in the solution. Thimerosal was added as a preservative and sufficient amount of distilled water to make 1 liter of solution. The solution may be sterilized by forcing through a 0.22 micron cellulose acetate filter by means of a peristaltic pump, or alternatively, by use of nitrogen gas under positive pressure. The solution was effective in removing tear film deposits from lenses.

EXAMPLE II

An aqueous contact lens cleaning and conditioning solution was prepared with the following formulation:

|  | Grams |
| --- | --- |
| Tetronic 1107 | 1.000 |
| Sodium Chloride | 6.750 |
| Boric Acid | 4.420 |
| Sodium Borate | 0.875 |
| $Na_2$ EDTA | 1.000 |
| Sorbic Acid | 1.000 |
| Dist. Water qs | 1 liter |

The above formulation was prepared by the method described in Example I, except the sorbic acid preservative was dissolved in the sodium borate solution before the $Na_2$ EDTA. Subsequently, the $Na_2$ EDTA and boric acid were dissolved with the sodium chloride. This solution was effective in removing tear film deposits from contact lenses.

EXAMPLE III

A cleaning and conditioning solution is prepared with the following formulation:

|  | Grams |
| --- | --- |
| Tetronic 1508* | 20.000 |
| Sodium Chloride | 6.750 |
| Boric Acid | 4.420 |
| Sodium Borate | 0.875 |
| $Na_2$ EDTA | 1.000 |
| Thimerosal (10 ppm) | 0.010 |
| Dist. Water qs | 1 liter |

*Flake grade, molecular weight 27,000, 80% (wt.) poly(oxyethyline)

The above formulation which is effective in cleaning both hard and soft contact lenses may be prepared using the method described in Example I.

EXAMPLE IV

Prophylactic Cleaning (High Temperature).

Separate artificial tear solutions were first prepared. The first solution was a clear-colorless protein solution containing lysozyme in a concentration of 0.2 grams/100 ml of electrolyte. The electrolyte was a stock solution prepared from sodium bicarbonate 2.2 gpl, sodium chloride 7 gpl, calcium chloride 0.005 gpl and potassium chloride 1.5 gpl. The second was a lipid solution containing trilinolein in an amount of five (5) drops per 100 ml of electrolyte. Because the lipid has a tendency to separate in solution, agitation means were used to maintain in a dispersed state. A control solution was also prepared containing 0.9 percent (w/v) sodium chloride.

Eight (8) polymacon soft contact lenses commercially available from Bausch & Lomb under the registered trademark SOFLENS were soaked in the artificial tear solutions for 30 to 60 minutes at room temperature. Four (4) of the soft lenses were soaked in the protein solution and four (4) in the lipid solution. After removing from the artificial tear solutions, one-half o the lenses were placed in a contact lens heat disinfecting unit available from Bausch & Lomb under the registered trademark ASEPTRON. The lens cases of the heat disinfecting unit were filled with the cleaning solution of Example I and the lenses inserted. Multiple soaking and heat disinfecting cycles were performed on the lenses. The heat disinfecting unit has a pre-programmed heating cycle which brings the temperature of the cleaning solution up to about 80°–90° C. for at least 10 minutes. At the conclusion of the heating cycle, the unit automatically shuts-down for cooling.

The remaining half of the lenses soaked in the tear solutions were placed in the heat disinfecting units filled with the control solution. The heat disinfecting units were turned on and allowed to go through their pre-programmed cycle.

At the conclusion of all the cleaning cycles, the lenses were examined under a Bausch & Lomb Stereo-Zoom ™ light microscope at 10× magnification for inspecting the surfaces of the lenses for film build-up. The lenses were also examined under a Bausch & Lomb brand Spectronic 2000 Model Ultraviolet/Visible Spectroscope at the visible light range of 500 nm for lens clarity and under ultraviolet light to identify protein build-up at 280 nm. The results of the inspections are provided in Table 1 below.

TABLE 1

| Tear Solution | Soaking/Cleaning Cycles | Cleaning Solution | Deposit Formation |
|---|---|---|---|
| Protein | 3 | 0.1% Tetronic 1107 | none |
| Protein | 3 | Control | very light |
| Lipid | 5 | 0.1% Tetronic 1107 | none |
| Lipid | 5 | Control | heavy |

EXAMPLE V

Prophylactic Cleaning (Room Temperature).

Twenty (20) polymacon soft contact lenses were soaked for 30 to 60 minutes at room temperature in the artificial protein containing tear solution described in Example IV. An additional eight (8) polymacon soft contact lenses were soaked for the same time period in the lipid-containing artificial tear solution. At the completion of the soaking cycle, half of the lenses from each of the artificial tear solutions were then soaked in isotonic saline control solution, and the remaining half soaked for 30 to 60 minutes in Tetronic 1107-containing cleaning solutions of varying concentrations prepared according to the formulation of Example I. The cleaning solutions were room temperature. Subsequently, all the lenses were heated disinfected in isotonic saline solution using ASEPTRON heat disinfecting units. The foregoing soaking, cleaning and disinfecting steps were repeated several times (cycle) and examined by light microscopy and ultraviolet/visible light spectroscopy. The results are provided in Table 2 below.

TABLE 2

| Tear Solution | Soaking/Cleaning Cycles | Cleaning Solution | Deposit Formation |
|---|---|---|---|
| Protein | 5 | 0.5% Tetronic 1107 | very light |
| Protein | 5 | 1.0% Tetronic 1107 | none |
| Protein | 5 | 2.5% Tetronic 1107 | none |
| Protein | 5 | 5.0% Tetronic 1107 | none |
| Protein | 5 | Control | very light |
| Lipid | 5 | 2.5% Tetronic 1107 | none |
| Lipid | 5 | Control | medium to heavy |

Tables 1 and 2 demonstrate the effectiveness of the surfactant based conditioning solutions in preventing the development of tear film deposits on contact lenses at ambient and elevated temperatures.

EXAMPLE VI

The cleaning and conditioning solutions of the type set forth in Example I containing Tetronic 1107 were tested for lens compatibility. The objective was to determine if the solutions caused any deformation of the lens.

In the first experiments, a group of two lenses were placed in the solution of Example I and inserted in an ASEPTRON heat disinfecting unit. Similar experiments were conducted using higher strength cleaning solutions containing Tetronic surfactant. Further lens compatibility studies were conducted at room temperature whereby Tetronic surfactant containing solutions ranging in percentages from 0.5 to 5 percent were employed. Compatibility of the surfactants with soft contact lenses is reported in Table 3 below.

TABLE 3

| Surfactant | Room Temperature | High Temperature | Lens Compatibility |
|---|---|---|---|
| Tetronic 1107 0.1% | | X | no lens deformation |
| Tetronic 1107 0.2% | | X | no lens deformation |
| Tetronic 1107 0.5% | X | X | no lens deformation in each instance |
| Tetronic 1107 1.0% | X | | no lens deformation |
| Tetronic 1107 2% | X | | no lens deformation |
| Tetronic 1107 5% | X | | no lens deformation |

EXAMPLE VII

A series of laboratory experiments were conducted to evaluate the performance of several surfactant solutions in dissolving denatured protein. For each experiment, a 0.4 percent aqueous albumin solution was prepared by heating to about 125° F. The protein test solution was turbid. Six individual 5 ml samples containing 2.5 ml protein solution and 2.5 ml surfactant solution were treated at ambient temperature conditions and examined after five minute, two hour and 24 hour intervals. A clear solution indicates the denatured protein was completely dissolved. The results of the experiments are provided in Table 4 below.

TABLE 4

| Surfactant | Concentration | 5 Minutes | 2 Hours | 24 Hours |
|---|---|---|---|---|
| Tetronic 1107 | 10% | Clear | Clear | Clear |
| Tetronic 1107 | 3% | Turbid | Clear | Clear |
| Myrj 52* | 10% | Turbid | Turbid | Turbid |
| Myrj 52 | 3% | Turbid | Turbid | Turbid |
| Miranol C2M** | 3% | Clear | Clear | Clear |
| Miranol C2M | 30% | Clear | Clear | Clear |
| Papain Enzyme Tablet (Allergan) | | Clear | Clear | ***Turbid | triethanolamine, chlorhexidine and chlorhexidine gluconate.

EXAMPLE VIII

Several different surfactant solutions were tested to determine their effectiveness in removing existing tear film deposits ("heroic"), inhibiting the formation of tear film deposits on soft contact lenses (prophylactic) and compatibility of the lenses in the various solutions. Artificial tear solutions were applied to the lenses using previously described methods. Performance was judged by means of light microscopy and ultraviolet light/visible spectroscopy methods. Each of the test solutions had the following formulation:

Surfactant . . . 0.1%
Sodium borate buffer to maintain pH at about 7.2
Tonicity adjusted with isotonic saline containing 0.9% sodium chloride
Distilled water qs . . . 1 liter

TABLE 5

| Surfactant | Solution Compatibility | CLEANING (HIGH TEMPERATURE) | | | |
|---|---|---|---|---|---|
| | | Heroic | | Prophylactic | |
| | | Protein | Lipid | Protein | Lipid |
| Amidox ® C5 - Ethoxylated alkyloamide, nonionic - Stepan Chemical | C | N | Y-1* | Y-S | Y |
| Brij ® 35 - Polyoxyethylene (23) lauryl ether, nonionic - ICI Americas | C | N | Y-1 | Y-S | Y |
| Triton ® X-100 - Octylphenoxy polyethoxy ethanol, nonionic - Rohm & Haas | C | N | Y-1 | N | Y |
| Plurafac ® A-38 - Oxyethylated straight chain alcohol, anionic - BASF Wyandotte | N | | | | |
| Atlas ® G-2162 - Polyoxyethylene propylene glycol stearate, nonionic - ICI Americas | N | | | | |
| Myrj ® 52 - Polyoxyl (40) stearate USP, nonionic ICI Americas | N | | | | |
| Amphosol ® CA - Coco amido butaine, amphoteric - Stepan Chemical | C | N | Y-1* | N | Y |
| Miranol ® C2M - 2-cocyl-1-(sodium carboxymethyl)-1-[(sodium carboxymethyoxy)ethyl]-2-imidazolinium hydroxide, amphoteric Miranol Chemical Co. | C | Y-S | Y-1 | Y-M | Y |
| Pluronic ® F-127 - Poly(ethylene oxide) condensate, nonionic, BASF Wyandotte | C | N | Y-1* | Y-S | N |
| Makon ® 8 - Alkylphenoxy polyethylene ethanol, nonionic - Stepan Chemical | N | | | | |
| Tetronic ® 1107 | C | N | Y-1 | Y-E | Y |

Compatibility:
C = Compatible;
NC = Not Compatible
Cleaning:
Y = Clean
N = No cleaning
Y-S = Slight cleaning ability
Y-M = Medium cleaning ability
Y-E = Excellent cleaning ability
*Number of cleaning cycles required to achieve result.

*Polyoxyl (40) Stearate U.S.P. (non-ionic) - ICI Americas
**2-cocyl-1-(sodium carboxymethyl)-1-[(sodium carboxymethoxy)ethyl]-2-imidazolinium hydroxide (amphoteric) Miranol Chemical Company
***Turbidity due to papain enzyme becoming denatured.

The lens cleaning solutions containing Miranol surfactant were found to be incompatible with certain preservatives, such as benzalkonium chloride, alkyl

EXAMPLE IX

Contact lens cleaning solutions are prepared with the following formulations:

|  | Soln. A | - Grams - | Soln. B |
| --- | --- | --- | --- |
| Polyvinyl Alcohol | 10.0 |  | 10.0 |
| Na₂ EDTA | 1.0 |  | 1.0 |
| Sodium Chloride | 5.9 |  | 5.9 |
| Tetronic 1107 | 10.0 |  | 10.0 |
| *Polysorbate 20 | 2.5 |  | — |
| Benzalkonium Chloride | 0.2 |  | 0.2 |
| Phosphate Buffer to ph | 7.4 |  | 7.4 |
| Distilled Water qs | 1.0 liter |  | 1.0 liter |

*mixture of laurate esters of sorbitols and sorbitol anhydrides condensed with 20 moles of ethylene oxide.

Twenty silafocon A hard gas permeable contact lenses are coated with denatural solution of lysozyme protein. The lenses are then examined by ultra violet spectroscopy for light transmission. Ten of the lenses are then cleaned with Solution A by rubbing between the forefinger and palm for 30 seconds. The remaining ten lenses are cleaned with Solution B in the same manner. After cleaning, the lenses are then examined by ultra violet spectroscopy. The ten lenses cleaned with Solution A had a post cleaning average percent transmission value of 91.8%, a 14.5% increase in transmission. Similar values are obtained with Solution B.

While the invention has been described in conjunction with specific examples thereof, this is illustrative only. Accordingly, many alternatives, modifications and variations will be apparent to those skilled in the art in light of the foregoing description, and it is therefore intended to embrace all such alternatives, modifications and variations as to fall within the spirit and broad scope of the appended claims.

What is claimed is:

1. An aqueous composition for effectively cleaning and conditioning contact lenses at ambient and elevated temperature conditions, consisting essentially of
   (a) from about 0.01 to about 15 weight percent of a poly(oxypropylene)-poly(oxyethylene) adduct of ethylene diamine having a molecular weight from about 7500 to about 27,000 wherein at least 40 weight percent of said adduct is poly(oxyethylene).
   (b) a germicidal agent in a sufficient amount of preserve sterility of the composition, and
   (c) water, said composition being free of amounts of thickening agents which materially alter its viscosity.

2. The composition of claim 1 wherein the molecular weight of the adduct is from about 10,000 to about 20,000 and from about 40 to about 80 weight percent of the adduct is poly(oxyethylene).

3. The composition of claim 2 wherein the molecular weight of the adduct is from about 12,000 to about 19,000 and from about 60 to about 80 weight percent of the adduct is poly(oxyethylene).

4. The composition of claim 2 wherein the adduct is present in an amount from about 0.1 to about 5 weight percent.

5. The composition of claim 4, including a tonicity agent.

6. The composition of claim 5, including a buffering agent.

7. The composition of claim 6 wherein the germicidal agent is thimerosal.

8. The composition of claim 6 wherein the germicidal agent is sorbic acid.

9. An aqueous composition for inhibiting the formation of tear film deposits on contact lenses, consisting essentially of
   (a) at least 0.01 weight percent of poly(oxypropylene)-poly(oxyethylene) adduct of ethylene diamine having a molecular weight from about 10,000 to about 20,000 wherein at least 40 weight percent of said adduct is poly(oxyethylene),
   (b) a germicidal agent in a sufficient amount to preserve the sterility of the composition,
   (c) a tonicity agent, and
   (d) water, said composition being free of thickening agents which materially alter its viscosity.

10. The composition of claim 9 wherein the molecular weight of the adduct is from about 12,000 to about 19,000 and at least 60 weight percent of the adduct is poly(oxyethylene).

11. An aqueous composition for efficient cleaning of tear film build-up and debris from soft contact lenses by cold soaking or heat disinfecting methods, said composition consisting essentially of
   (a) from about 0.1 to about 5 weight percent of poly(oxypropylene)-poly(oxyethylene) adduct of ethylene diamine having a molecular weight ranging from about 12,000 to about 19,000 wherein at least 60 weight percent of the adduct is poly(oxyethylene),
   (b) a germicidal agent in a sufficient amount to preserve the sterility of the composition,
   (c) a sequestering agent,
   (d) a tonicity agent,
   (e) a buffering agent in a sufficient amount to maintain the pH of the composition in a range of about 6.5 to 7.8, and
   (f) water, said composition being free of thickening agents which materially alter its viscosity.

12. The composition of claim 11 wherein the adduct has a molecular weight of approximately 14,500 and about 70 weight percent of the adduct is poly(oxyethylene).

13. The method of cleaning and conditioning contact lenses which comprises contacting the lenses with the composition of claim 1 for a sufficient time period to remove film build-up and any debris, said cleaning and conditioning being conducted at either ambient or elevated temperature conditions.

14. The method of claim 13, including the step of rinsing the cleaned and conditioned lenses with a saline solution.

15. The method of claim 14 wherein cleaning and conditioning of the lenses is carried out at temperatures ranging from about 20° C. to about 90° C.

16. A method of inhibiting the formation of tear film build-up on soft contact lenses which comprises contacting the lenses with the composition of claim 5, said cleaning being carried out by cold soaking or heat disinfection.

17. The method of claim 16 wherein the lenses are conditioned by heat disinfection at a temperature of at least 80° C.

18. A method of cleaning and conditioning soft contact lenses which comprises contacting the lenses with the composition of claim 11 for a sufficient time period to remove film build-up, said cleaning and conditioning being conducted at temperatures ranging from about 20° C. to about 90° C.

19. The method of claim 18, including the step of rinsing the cleaned and conditioned lenses with a saline solution.

* * * * *